(12) United States Patent
Strowe et al.

(10) Patent No.: US 6,277,099 B1
(45) Date of Patent: Aug. 21, 2001

(54) MEDICATION DELIVERY PEN

(75) Inventors: Robert J. Strowe, Ramsey, NJ (US); John E. Burbank, III, Ridgefield, CT (US); Jay D. Packman, Edgewater, NJ (US); Robert C. Uschold, Monroe, NY (US); Antonio A. Bendek, Vernon, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/370,058

(22) Filed: Aug. 6, 1999

(51) Int. Cl.[7] .................................................. A61M 5/00
(52) U.S. Cl. ............................... 604/207; 604/186
(58) Field of Search .................................... 604/187, 200, 604/207, 208, 211, 218, 223, 228, 232, 234, 235, 244, 246, 131, 186, 152, 154

(56) References Cited

U.S. PATENT DOCUMENTS 5,279,585 * 1/1994 Balkwill .
5,593,390 * 1/1997 Castellano et al. .

\* cited by examiner

*Primary Examiner*—Sharon Kennedy
*Assistant Examiner*—Catherine Serke
(74) *Attorney, Agent, or Firm*—Alan W. Fiedler

(57) ABSTRACT

A medication delivery pen includes a housing having an actuator disposed in the proximal end of the housing for setting and administering a dosage of medication, a medication-containing cartridge assembly having a cartridge with a pierceably sealed distal end, an open proximal end removably attachable to the distal end of the housing, and a piston in sliding, fluid tight engagement within the cartridge. A drive mechanism is coupled between the actuator and the cartridge to exert an axial force on the piston to inject the set dosage of medication. The actuator triggers the drive mechanism to administer the injection of medication held in the cartridge and a processor is coupled to the actuator to determine a value equal to the dosage set by the actuator. The drive mechanism includes a pair of half nuts in rotational engagement with the actuator, a non-rotatable lead screw having a distal end for exerting the axial force on the piston to inject the set dosage of medication, a proximal end, and threads extending between the proximal and distal ends. The nuts open and close radially to selectively engage with the threads of the lead screw for axially advancing along the lead screw upon rotation of the actuator.

23 Claims, 12 Drawing Sheets

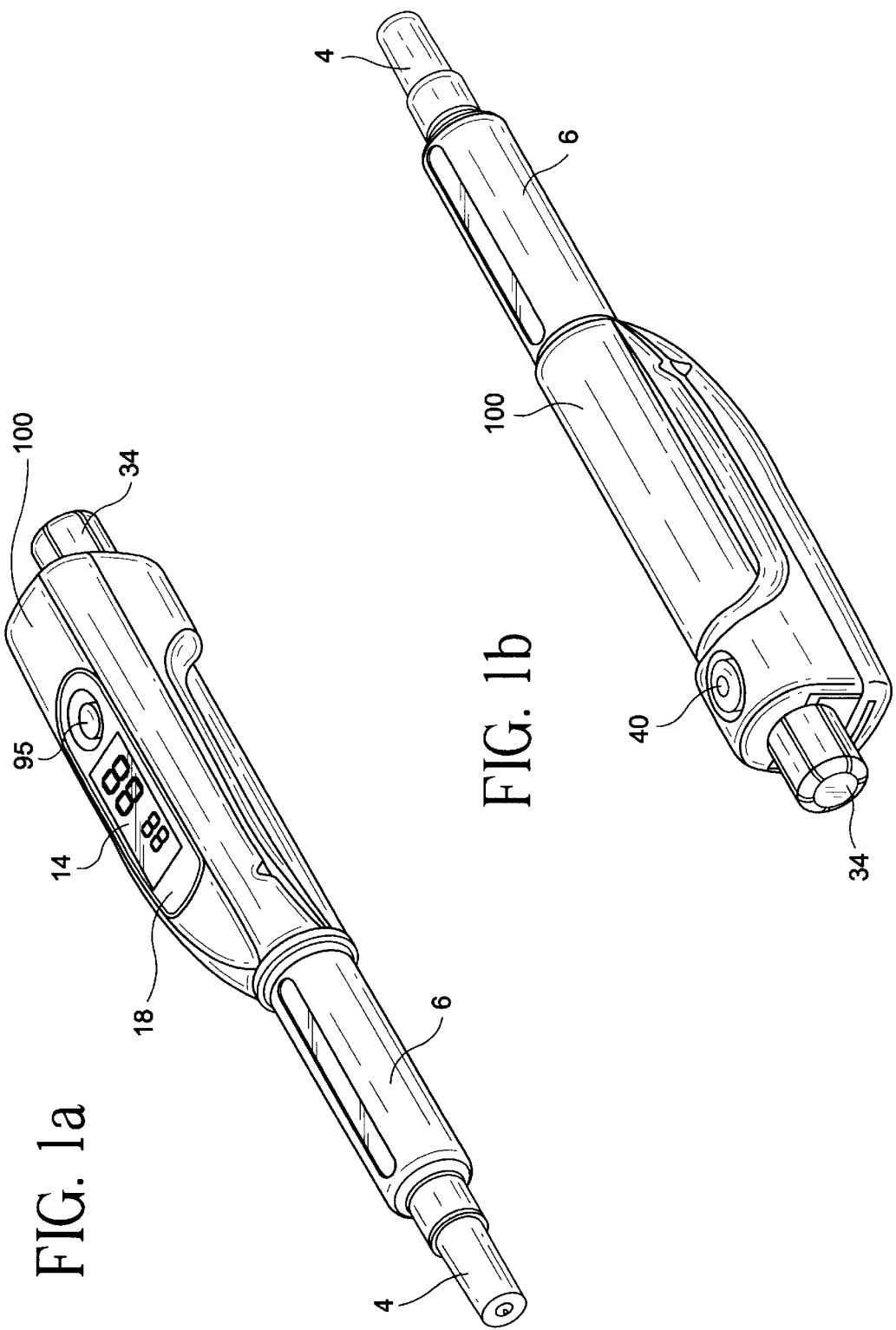

MEDICATION DELIVERY PEN

BACKGROUND OF THE INVENTION

1. Field of the Invention

The subject invention relates to a diagnostic and medication delivery system having a medication delivery pen, blood monitoring device and a lancer removably mounted in a common housing.

2. Description of Related Art

Home diabetes therapy requires the patient to carry out a prescribed regimen that involves self-testing blood glucose levels and administering an appropriate dose of insulin. Insulin has traditionally been injected by a hypodermic syringe, which suffers from numerous drawbacks. For example, syringes are not preloaded with medication, requiring the user to carry a separate medical vial. Syringes also require a degree of dexterity and sufficient visual acuity on the part of the patient to line up the needle of the syringe with the rubber septum on the medical vial and to ensure that the syringe is loaded with the proper dosage. As a result, unintentional needle pricks commonly occur.

To overcome the drawbacks of syringes, medication delivery pens have been developed, which facilitate the self-administration of medication such as insulin. Such delivery pens use prepackaged insulin and may be used repeatedly until the medication is exhausted. Mechanical and electronic pens are available. Electronic pens incorporate electronic circuitry that sets and/or indicates the appropriate dosage of insulin and stores data for subsequent downloading such as the time, date, amount of medication injected, etc.

In additional to downloading data, the electronic capabilities of such pens can also be used to mechanically simplify the pen and enhance the pen's ease of use. For example, some known pens employ an interlock mechanism to prevent actuation of the injection button when the medication cartridge is not properly connected to the pen so that an overdose does not occur. The interlock mechanism is relatively complex from both a mechanical perspective and a patient perspective. The electronic detection of the presence or absence of a properly connected cartridge can eliminate the need for such an interlock.

Additional mechanical improvements to medication delivery pens are also desirable to increase reliability and ensure that the proper dosage of medication is delivered. For example, known pens must undergo a priming process every time they are loaded with a cartridge. Priming ensures that the drive mechanism is in contact with the piston inside the cartridge so that the full axial travel of the drive mechanism is used to inject medication rather than being used in part to approach and contact the piston. If priming is not properly performed by the user, the actual dosage of medication that is delivered will not equal the desired dosage. Accordingly, there is a need to eliminate or reduce the amount of priming that the user must perform.

SUMMARY OF THE INVENTION

The subject invention relates to an electronic medication delivery pen which has mechanical features that reduce the amount of priming that must be performed, eliminates the need for an interlock mechanism to prevent overdosing, increases the reliability of the drive mechanism, and ensures that the full dosage of medication is delivered upon injection.

In accordance with the present invention, a medication delivery pen includes a housing having opposing proximal and distal ends. An actuator is disposed in the proximal end of the housing for setting and administering a dosage of medication. A medication-containing cartridge assembly includes a cartridge having a pierceably sealed distal end, an open proximal end removably attachable to the distal end of the housing, and a piston in sliding, fluid tight engagement within the cartridge. A drive mechanism is coupled between the actuator and the cartridge to exert an axial force on the piston to inject the set dosage of medication. The actuator triggers the drive mechanism to administer the injection of medication held in the cartridge. A processor is coupled to the actuator to determine a value equal to the dosage set by the actuator and a memory device is coupled to the processor to store the dosage value determined by the processor. The drive mechanism includes a pair of half nuts in rotational engagement with the actuator, a non-rotatable lead screw having a distal end for exerting the axial force on the piston to inject the set dosage of medication, a proximal end, and threads extending between the proximal and distal ends. The nuts open and close radially to selectively engage with the threads of the lead screw for axially advancing along the lead screw upon rotation of the actuator.

Because the half nuts advance along the lead screw, thus eliminating the need for a rotatable lead screw, the inventive medication delivery pen advantageously reduces the likelihood that components will improperly engage with one another due to their misalignment during operation.

In accordance with another aspect of the invention, a first spring is provided in the housing to bias the lead screw in the distal direction so that the lead screw remains in contact with the cartridge piston when the cartridge assembly is attached to the housing. This feature advantageously reduces the amount of priming that must be performed upon installation of a new cartridge.

In accordance with yet another aspect of the invention, a release nut is provided to engage with the lead screw at a location distally of the half nuts. The release nut is located at a first axial position when the cartridge is attached to the housing and a second axial position when the cartridge is removed from the housing. The release nut activates the processor so that the processor is in an operational state when the release nut is in the first axial position and is in a disabled state when the release nut is in the second axial position. Accordingly, since the pen will be automatically disabled when the cartridge is not properly inserted, the present invention advantageously avoids the need for a separate interlock mechanism.

In accordance with yet another aspect of the invention, at least one dial stop element couples the distal ends of the half nuts to the release nut so that the axial travel of the half nuts is limited to a minimum value, thereby limiting the injectable dosage of medication to a minimum value. Likewise, the dial stop element may also limit the axial travel of the half nuts to a maximum value, thereby limiting the injectable dosage of medication to a maximum value.

In accordance with another aspect of the invention, the actuator includes a rotatable knob and a plunger in rotational engagement with the rotatable knob. The plunger has a plurality of axial splines located on its distal end that define slots therebetween. The housing has at least one radially extending boss that aligns with the slots in select rotational states of the plunger to allow axial motion of the plunger and misaligns with the slots in other rotational states of the plunger to prevent axial motion of the plunger. The select rotational states of the plunger aligning with the boss correspond to an integer number of dosage units. This feature of the invention advantageously ensures that the user can only inject a whole number of units of medication.

BRIEF DESCRIPTION OF THE DRAWINGS

FIGS. 1(a) and 1(b) show perspective views of a medication delivery pen of the subject invention;

DETAILED DESCRIPTION

Figure 2A:
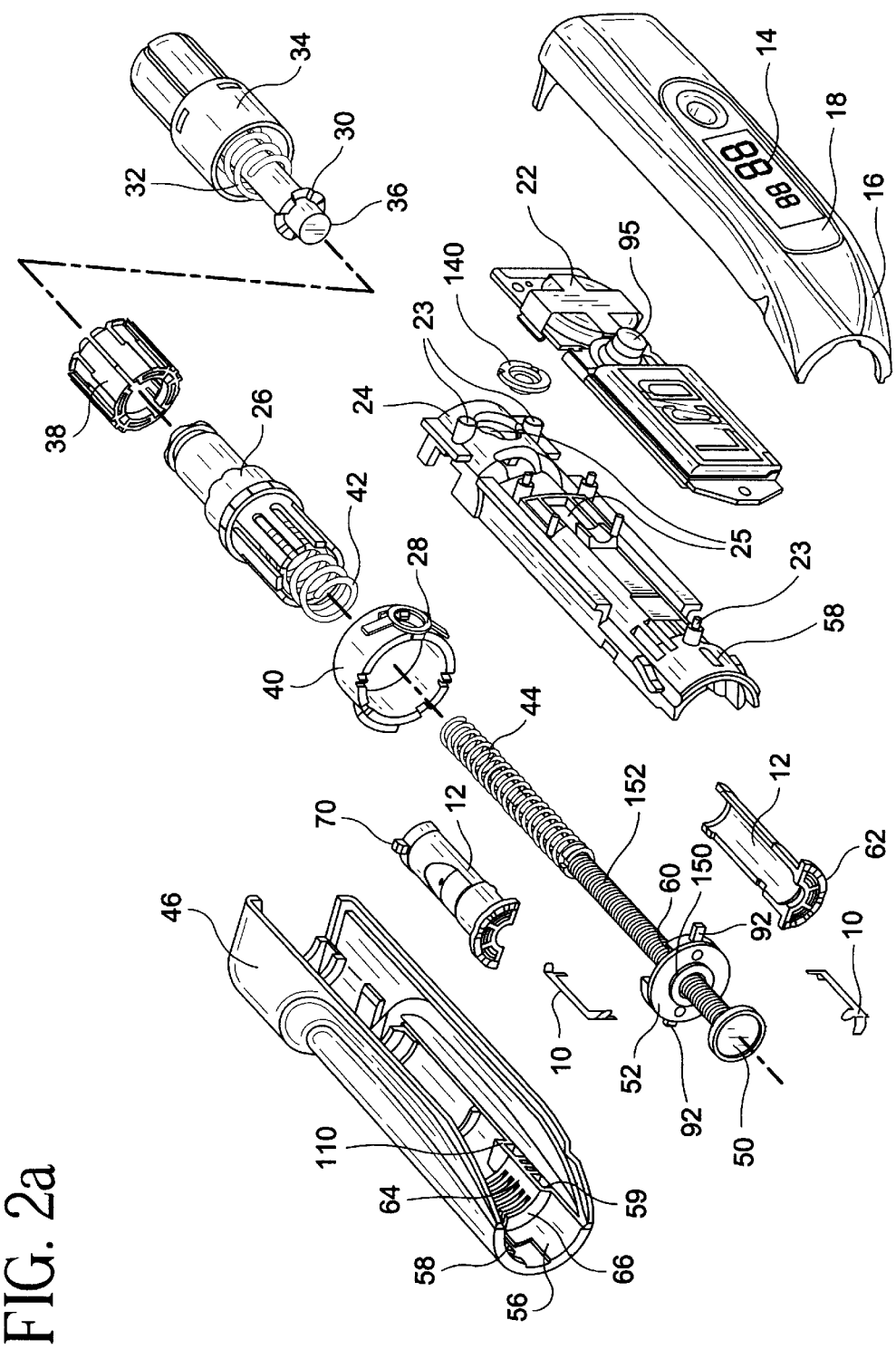
FIGS. 2(a) and 2(b) are exploded perspective views of the pen shown in FIG. 1 showing the details of the proximal and distal ends, respectively.
Figure 2B:
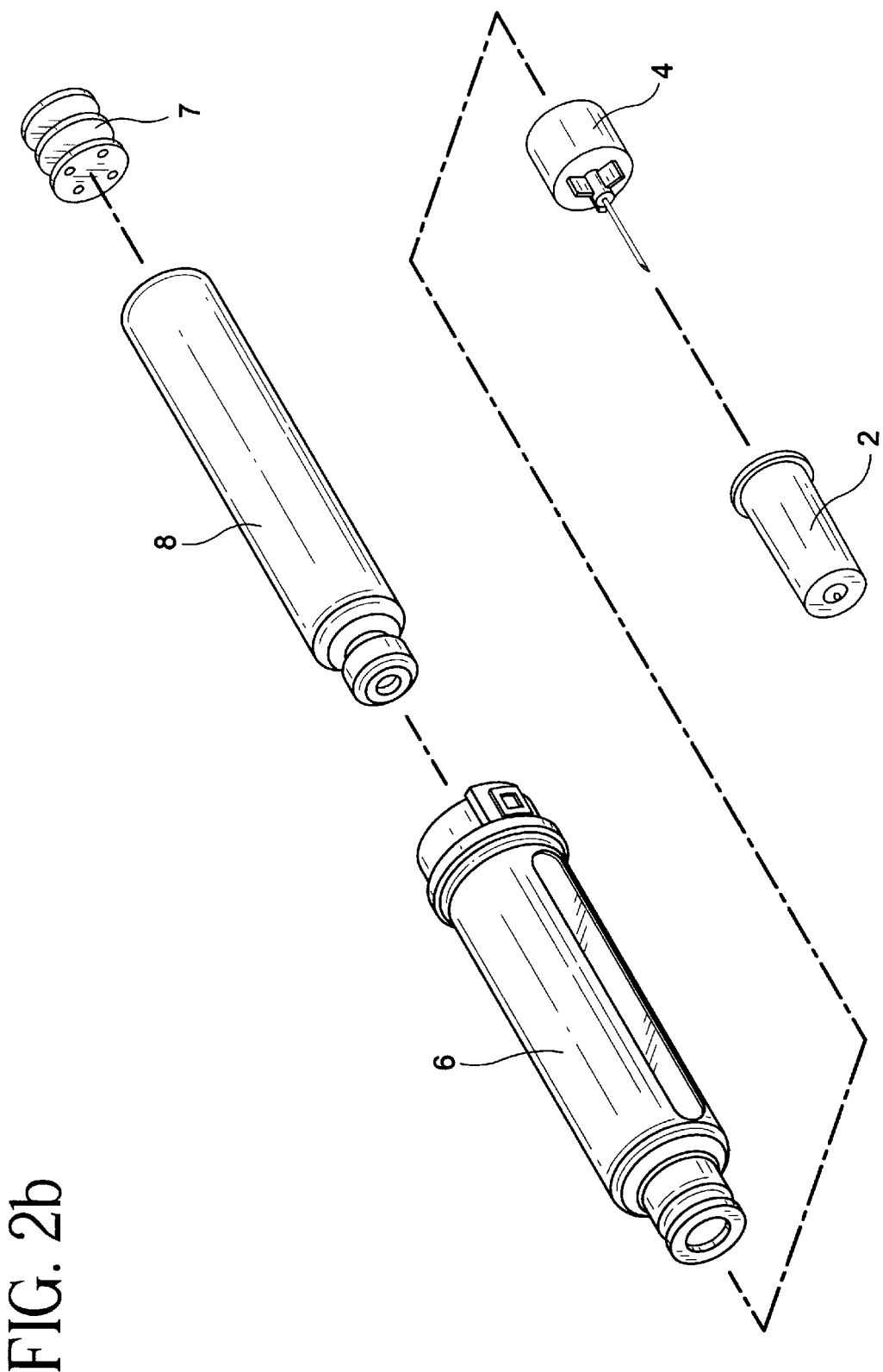

As shown in FIGS. 1 and 2, the medication delivery device includes a rotatable dose knob 34, housing 100, cartridge retainer 6, and needle assembly 4. A display 14 is visible through a window 18 in the housing 100. The overall operation of the medication delivery pen is as follows. First, a cartridge 8 is loaded within cartridge retainer 6, and cartridge retainer 6 is removably attached to housing 100. When the cartridge retainer 6 is removed from the housing 100, a lead screw 50 is forward biased by lead screw spring 44 to ensure that the distal end of the lead screw is always in contact with the cartridge piston 7 located in cartridge 8. As a result, the amount of priming that must be performed by the user upon inserting a new cartridge 8 is minimized. The needle assembly 4 is affixed to the end of cartridge 8. Fluid communication is accordingly established between the injection portion of needle assembly 4, and the interior of cartridge 8. Eject button 40 is pressed to release dose knob 34. Once the appropriate dosage is set by rotation of dose knob 34, dose knob 34 is depressed, exerting a force upon piston 7, which is movably positioned within cartridge 8. Piston 7 displaces fluid within cartridge 8, causing its injection into body tissue through needle assembly 4.

Figure 3A:
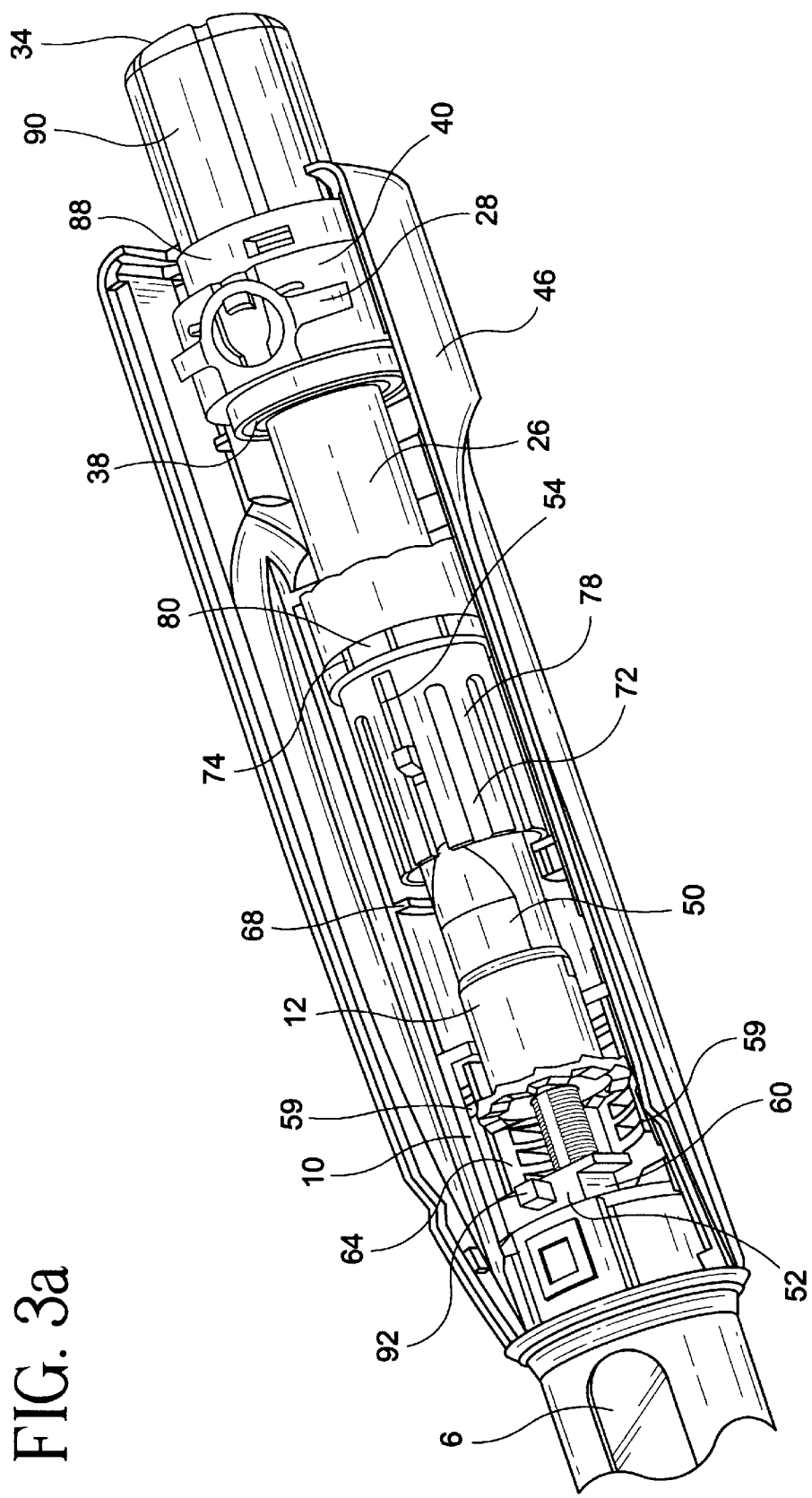
FIG. 3(a) shows the drive mechanism situated in the bottom case of the pen housing and FIG. 3(b) shows the bottom case without the drive mechanism to illustrate the various bearings surfaces that operatively interact with the drive mechanism.
Figure 3B:
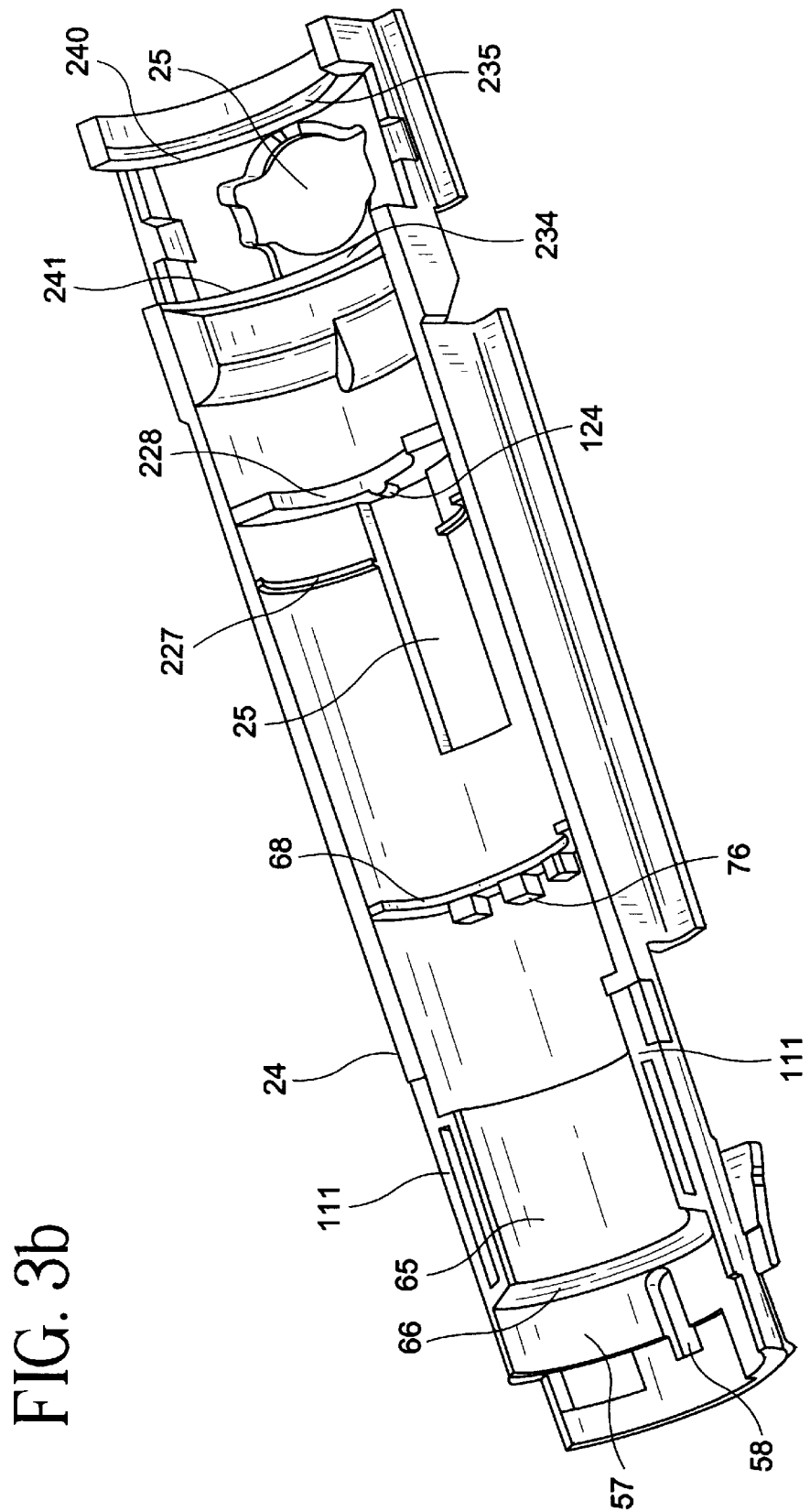

Referring to FIGS. 2 and 3, a dosing mechanism includes dose knob 34, clutch spring 32, dose knob insert 38, plunger 26, half nuts 12, lead screw 50, and keyed release nut 52, which are collectively used to set the dosage of medication that is to be injected. The housing 100 includes bottom case 46, middle case 24, and top case 16. The dosing mechanism is situated between the bottom and middle cases 46 and 24. As detailed below, the interior surface of middle and bottom cases 24 and 46 provide working surfaces along which the various components of the dosing mechanism are operable. The dose knob insert 38 is attached to the dose knob 34. As detailed below, clutch spring 32 exerts an axial load to ensure a positive rotational engagement between the dosing knob 34 and plunger 26. As a result, the plunger 26 is driven rotationally when the user dials the dosing knob 34. The plunger 26 includes a hollow, generally cylindrical body having a series of axial slots 72 extending from its distal end. Axial slots 72 define a series of axial splines 78 between adjacent ones of the slots 72. Two of the slots, 180° apart, are through-slots 54. The intermediate surface portion 80 of plunger 26 has an outer diameter that is larger than the diameter of the plunger 26 along splines 78. A plurality of splines 74 project radially from surface 80 of plunger 26.

A pair of half nuts 12 each have a semi-cylindrical body having a flange 62 on its distal end and a radially projecting boss 70 on its proximal end. Bosses 70 are disposed in the axial slots 54 of plunger 26 so that half nuts 12 and plunger 26 are in rotational engagement with one another. Accordingly, as the plunger 26 rotates upon rotation of dosing knob 34 by the user, half nuts 12 axially advance along lead screw 50 until the desired dosage is reached. A keyed release nut 52 located on lead screw 50 has tabs 152 that fit inside slots 150 on the lead screw 50 so that release nut 52 guides the lead screw 50 axially and prevents it from rotating. (See FIGS. 4a and 4b)

Bottom and middle cases 46 and 24 provide bearing surfaces 64 and 65 for the half nuts 12, bearing surfaces 56 and 57 for the keyed release nut 52, bearing surfaces 110 and 111 for the dial stop insert 10, bearing surfaces 227 and 228 for the plunger 26, bearing surfaces 240 and 241 for the eject button 40 and eject button spring 28, and bearing surfaces 234 and 235 for dose knob 34. The middle case 24 also provides anchoring posts 23 for the PC board assembly 22 and access ports 25 so that the electronics located on PC board assembly 22 can communicate with sensors co-located with the mechanical components.

Keyed release nut 52 has a pair of recesses 60 (see FIG. 4b) on its proximal face in which dial stop inserts 10 are situated. Dial stop inserts 10 and keyed release nut 52 travel in unison as the cartridge retainer 6 is inserted and removed from the body of the delivery device. The axial motion of the dial stop inserts is limited by bosses 59. As explained below, dial stop inserts 10 provide mechanical stops for minimum, i.e. zero, and maximum dosages. Upon removal of the cartridge retainer 6, keyed release nut 52 moves distally, allowing the half nuts 12 to also move distally under the action of half nut spring 42. As a result, the radially extending bosses 70 of half nuts 12 contact raised circumferentially extending surface 68 of bottom and middle cases 46 and 24 so that the half nuts 12 are prevented from further traveling in the axial direction and are forced to open radially to release the lead screw 50, thus allowing the system to be reset. Conversely, upon insertion of cartridge retainer 6, keyed release nut 52 moves in the proximal direction, forcing the half nuts 12 to advance along surface 66 of bottom and middle cases 46 and 24 so that the half nuts 12 close in the radial direction and engage with the lead screw 50.

The axial travel of keyed release nut 52 in either direction is limited by two pins 92 that engage with slots 58 formed in the bottom and middle cases 46 and 24. Slot 58 in body middle 24 is a through-hole slot while slot 58 in body bottom 46 is a recessed slot rather than a through-hole. Slots 58 also prevent rotational movement of the key nut 12. Half nut bearing surfaces 64 and 65 provide a bearing surface for the half nuts 12 when they are engaged with the lead screw 50

(which only occurs when the cartridge retainer 6 is attached to the housing 100). The axial travel of the half nuts 12 is limited by dial stop 10, as described below. As shown in FIG. 4(*a*) and 4(*b*), half nuts 12 each have a distal flange 62 that have a plurality of teeth. The teeth have a radial length, an axial thickness and are circumferentially located along the outer perimeter of flanges 62. The teeth are located on both the distal surface 61 and proximal surface 63 of the flange 62. As seen in FIG. 4(*a*), the teeth 161 on the distal surface 61 engaging the lower stop surface 9 of the dial stop insert 10 provides a stop so that the user cannot dial below zero. Similarly, as seen in FIG. 4(*b*), the teeth 163 on the proximal surface 63 engaging the upper stop surface 9 of the dial stop insert 10 provides a stop so that the user cannot dial above the maximum dose of the pen.

Figure 5B:
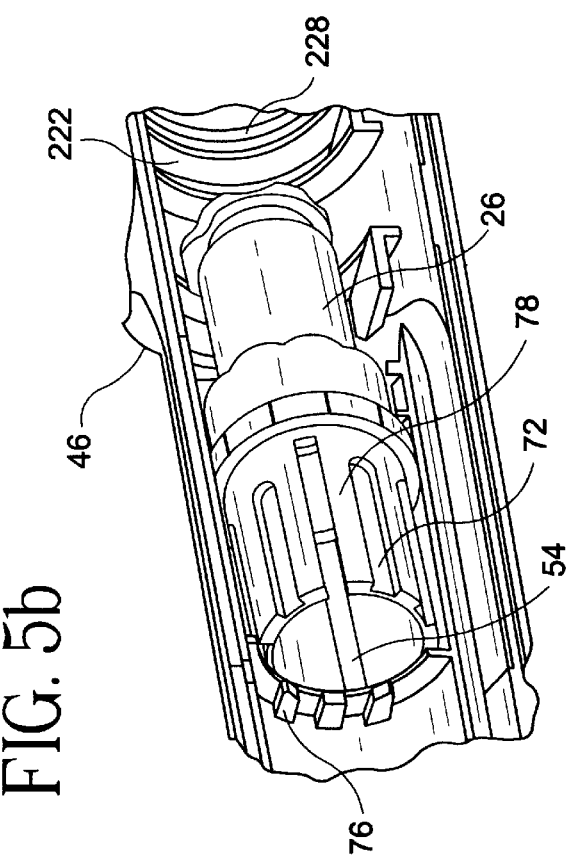
FIG. 5 shows a perspective view of the plunger situated in the pen housing when in a rotational orientation corresponding to an injectable state (FIG. 5a) and a noninjectable state (FIG. 5b) and the mechanism for biasing the plunger into an injectable state (FIG. 5c)
Figure 5A:
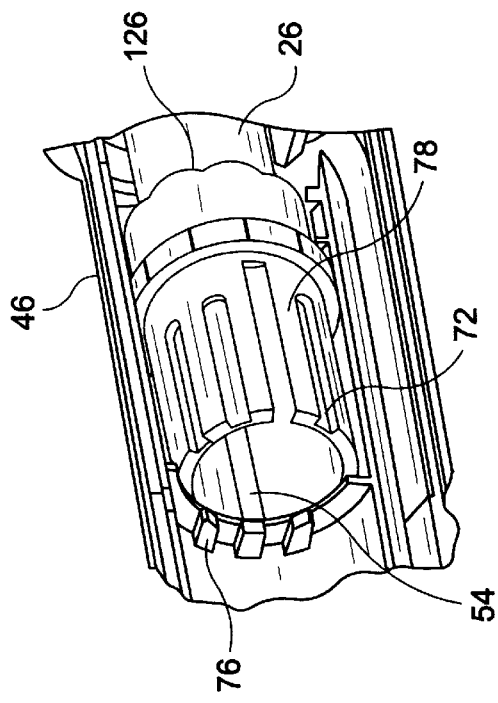
Figure 5C:
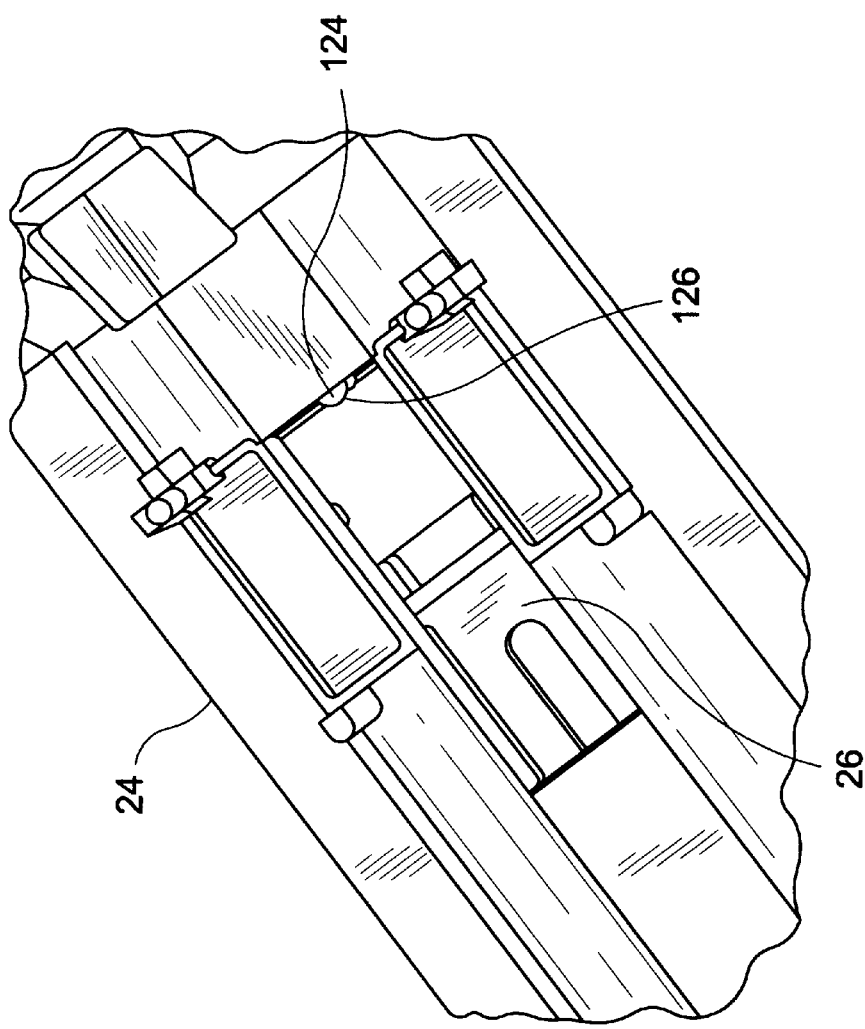

As shown in FIGS. 5(*a*)–(*c*), plunger 26 has a plurality of recessed slots 72 and 54 located on its distal end which define splines 78 between adjacent slots 72 and 54. Slots 72 and 54 are open on their distal end. A plurality of radially extending bosses 76 are located on bottom and middle cases 46 and 24. For an injection to occur, slots 72 and 54 must be radially aligned with bosses 76 (FIG. 5*a*). When the dosage is not set to an integer number of units (FIG. 5*b*) splines 78 are prevented from moving axially by bosses 76, thus preventing injection of fractional units. In described, slots 72 and 54 both perform the same function. Plunger 26 also has a plurality of angled radial slots 126 proximal to the splines 74. The number of angled radial slots 126 is equal to the number of slots 72 and 54. Tabs 124 are provided on the bottom case 46, middle case 24 and on the face 222 of bearing surface 228. When the plunger 26 is in the dosing mode, the half hut spring 42 biases the plunger 26 towards the bearing surface 228. The interaction of the angled radial slots 126 and the tabs 124 rotationally align the plunger 26 so that the plunger 26 is biased in a rotational state that aligns slots 72 and 54 with bosses 76.

Figure 6A:
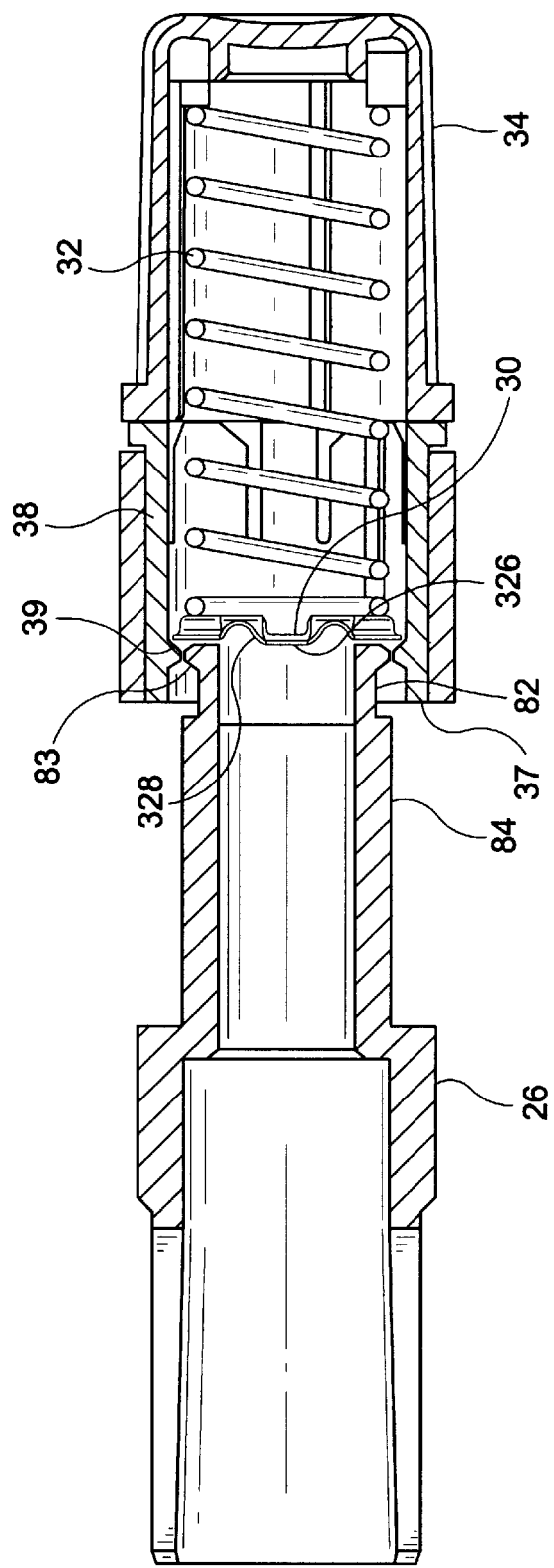
FIG. 6(a) shows the clutch arrangement employed in the drive mechanism of the pen and FIGS. 6(b) and 6(c) show the portions of the clutch arrangement formed on the plunger and the dose knob insert, respectively.
Figure 6C:
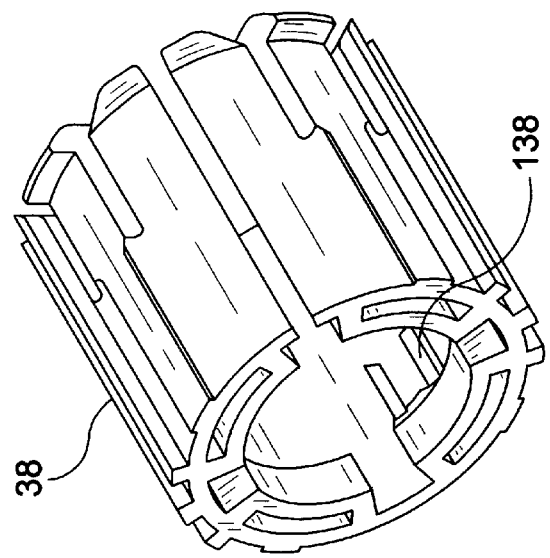
Figure 6B:
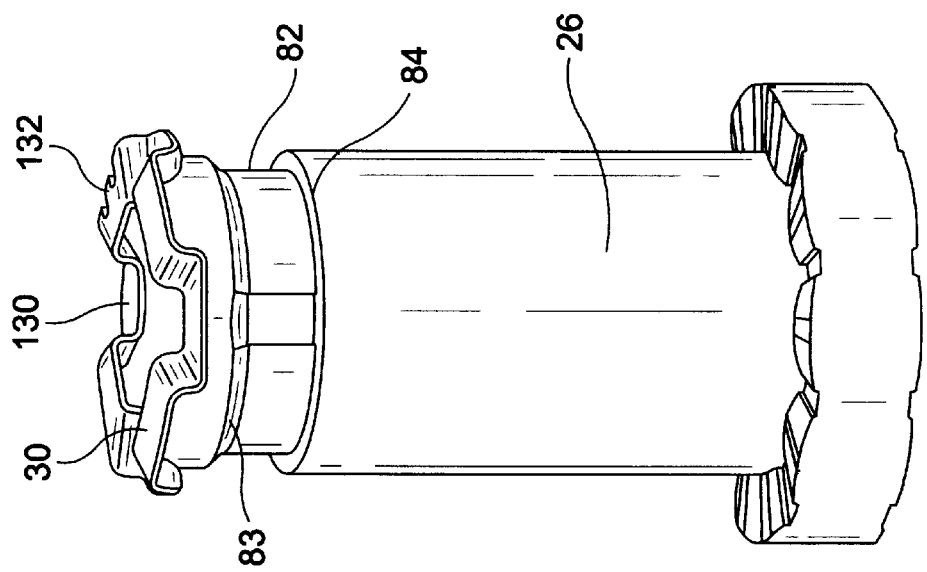

As shown in FIGS. 6(*a*) and 6(*b*), plunger 26 has a circumferential groove 82 located on its proximal end. Groove 82 has a distal wall 84 that serves as a bearing surface with the distal surface 37 of the dose knob insert 38 during injection. Groove 82 also has a proximal wall 83 that acts as a bearing surface with the angled surface 39 of the dose knob insert 38 when a dose is dialed. The plunger 26 has 4 radial slots 326 at its proximal end. The radial slots 326 have angled faces 328. A stepped clutch seat 30 has 4 radial splines 130. The stepped clutch disk also has two slots 132 that rotationally engage with two splines 138 located on the dose knob insert 38, which is in turn rotationally coupled to the dose knob 34. A clutch pumping spring 32 exerts an axial load on the stepped clutch seat 30 and the dose knob, assuring a positive rotational engagement between the dosing knob assembly, which includes the dose knob 34, dose knob insert 38, and the plunger 26. When the rotational movement of the half nuts 12 is restrained by the dial stop inserts 10, the splines 130 located on the stepped clutch disk 30 advance along the angled faces 328 of plunger 26, compressing the clutch pumping spring 32. As a result, the plunger 26 will not rotate, preventing damage to the mechanism that could be caused by excessive torque.

The dosage that is dialed by dose knob 34 is measured by a piezoelectric sensor, discussed below, that determines the number of rotations that the plunger 26 undergoes as the dose knob is rotated. Specifically, the piezoelectric sensor is activated by splines 74 located on an intermediate surface portion 80 of the plunger 26. The intermediate surface portion 80 of plunger 26 has an outer diameter that is larger than the diameter of boss 70 on half nuts 12 so that the bosses 70 do not interfere with the piezoelectric sensor.

An eject button 40 is accessible to the user via a hole in the bottom case 46. Eject button 40 locks dose knob 34 in its depressed state after completion of the injection so that the clutch spring can finish delivering the dose of medication, as described below. This is accomplished as follows. The eject button 40 is biased toward the bottom case 46 by eject button spring 28, which is housed in middle case 24. Eject button 40 is proximally biased by the eject button spring 28 and limited by the bearing wall 240. Dose knob 34 includes a distal end 88 that has a larger diameter than its proximal end 90. While the dose knob 34 is in its extended position, the eject button 40 is riding on the larger diameter distal end 88 of the dose knob 34. Dose knob 34 is proximally biased by the half nut spring 42. Accordingly, when the dose knob 34 is depressed, the eject button 40 snaps onto the smaller diameter proximal end 90 of the dose knob 34 so that the dose knob 34 is locked axially. A lead screw sleeve 36 is provided to prevent interaction between lead screw spring 44 and clutch pumping spring 32, which are coaxially located within dose knob 34.

Figure 4A:
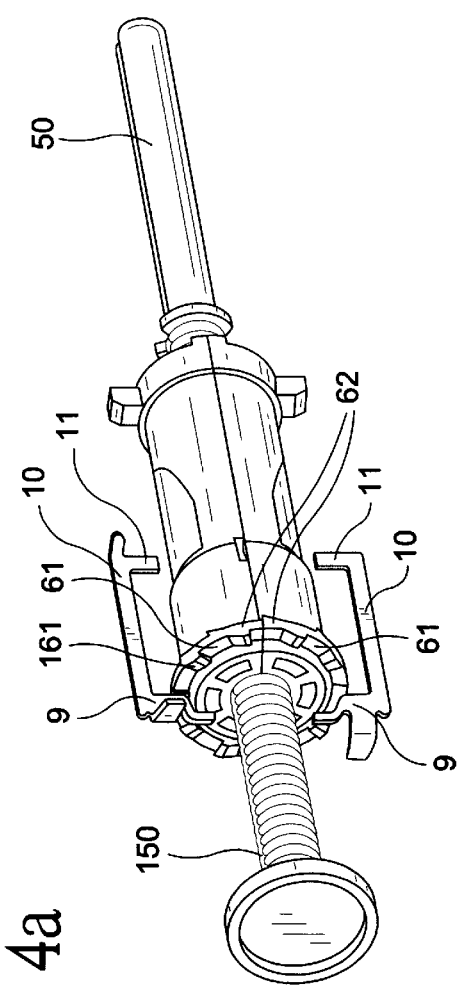
FIG. 4 shows a perspective view of the drive mechanism in which the half nuts and dial stops are positioned for maximum dosage (FIG. 4a) and minimum dosage (FIG. 4b)
Figure 4B:
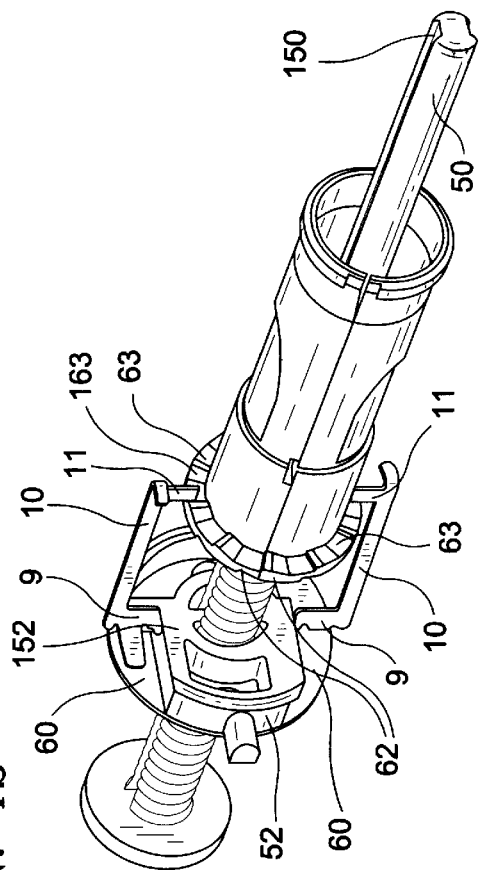

Once the eject button 40 locks dose knob 34 in its depressed state, clutch spring 32 serves to complete the distal movement of the plunger 26 and half nuts 12. This guarantees that the full dosage is delivered. The full dosage is delivered when the distal face 61 of flange 62 contacts the lower stop surface 9 of the dial stop insert 10 (FIG. 4*a*). At this time, the distal surface 37 of the dose knob insert 38 is no longer in contact with the distal surface 84 of groove 82, which is located on plunger 26. This configuration improves upon prior art medication delivery pens, which sometimes required the user to repeatedly depress dose knob 34 to ensure full delivery of the medication.

As previously mentioned, keyed release nut 52 has a pin 92 that extends in through-hole slot 58 of body middle 24. Pin 92 activates a cartridge removal switch on the PC board 22 so that the display indicates that the cartridge has been removed. Specifically, when pin 92 is situated towards the proximal end of slot 58, the switch is in its open state and the display is in its normal operational state. When pin 92 is situated against the distal end of slot 58, the switch is in its closed state and the display indicates that the cartridge has been removed.

Figure 7A:
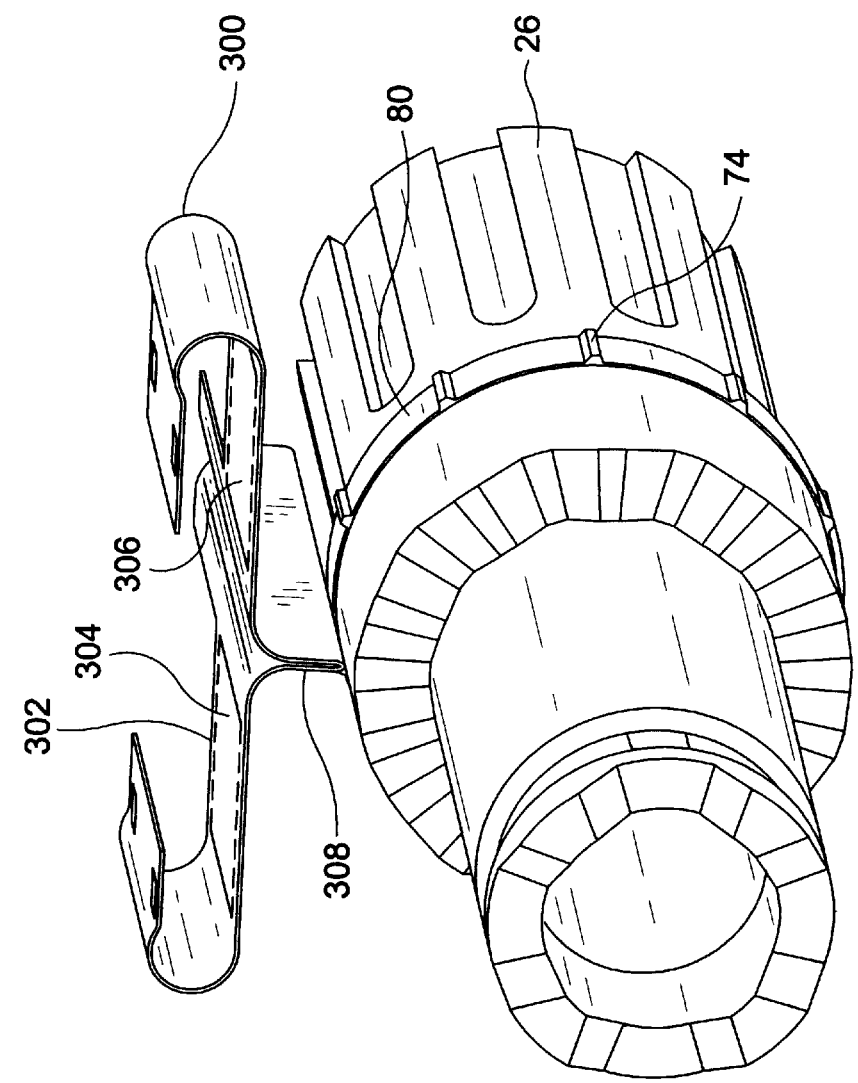
FIG. 7(a) shows a schematic diagram of the piezoelectric sensor arrangement that is used to determine the dosage that is set by rotation of the dose knob and FIGS. 7(b) and 7(c) show the deformation of the sensor arrangement when the plunger rotates clockwise and counter-clockwise, respectively.
Figure 7B:
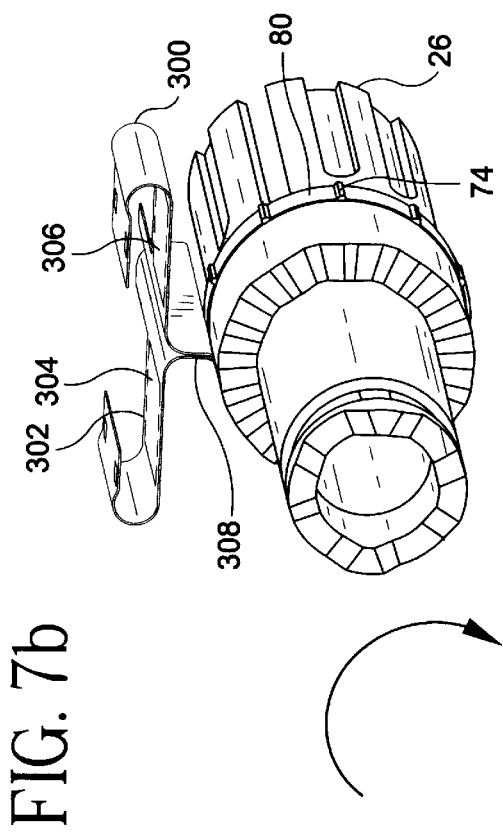
Figure 7C:
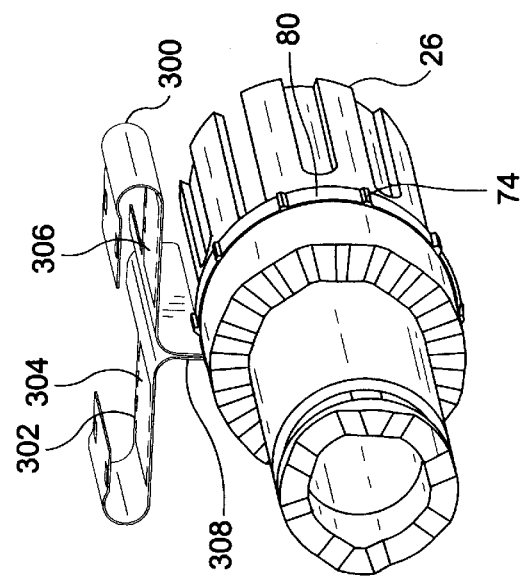

The dosage, which is set by rotation of dose knob 34, is measured by a piezoelectric sensor arrangement that interacts with the splines 74 on plunger 26. As shown in FIG. 7(*a*), the piezoelectric sensor 300 arrangement includes a flexible base 302 such as a spring. Disposed on one side of the base are two piezoelectric films 304 and 306 that are coplanar with the flexible base 302. A pawl 308 extends orthogonal from the side of the flexible base 302 opposite to the piezoelectric films 304 and 306. The pawl 308 is positioned along the flexible base 302 so that a plane through the pawl 308 and the flexible base 302 extends between the two films 304 and 306. The sensor arrangement is positioned with respect to the plunger 26 so that as the plunger 26 rotates the splines 74 engage with the pawl 308, which in turn causes deformation of the flexible base 302 (see FIGS. 7*b* and 7*c*). The deformation of the flexible base 302 causes a corresponding deformation of the piezoelectric films 304 and 306. The films 304 and 306 generate a pair of electrical signals each time the pawl 308 is released by one of the splines 74, based on direction of rotation and deformation of films 304 and 306. The curvatures of the deformed films are opposite to one another and depend on the direction in which the plunger 26 is rotating. For example, in FIG. 7(*b*) the plunger 26 is rotating in the clockwise direction and in FIG. 7(*c*) the plunger is rotating in the counter-clockwise direction. As shown, the curvatures of each film are opposite to one another in FIGS. 7(b) and 7(c). Since the curvatures of the films are always opposite to one another, they will generate electrical signals of opposite phase. In FIG. 7(b), for instance, film 304 may generate a positive signal while film 306 may generate a negative signal. In FIG. 7(c), however, the films will produce signals opposite in sign: film 304 will generate a negative signal and film 306 will generate a positive signal. Accordingly, the signs of the signals generated by the two piezoelectric films 304 and 306 can be used to distinguish between clockwise and counter-clockwise rotation. In addition, the absence of either signal identifies the failure of one of the films 304 and 306 and is used to identify and display a malfunction in the medication delivery pen.

The piezoelectric sensor will send the pair of electrical signals to the processor located on the PC board 22 each time the pawl 308 is released by one of the splines 74. Each pair of signals that is generated denotes a rotation of the dose knob 34 by a predetermined amount, and thus corresponds to a predetermined incremental increase or decrease in dosage. Since rotation of the dose knob 34 in one direction increases the dosage and rotation of the dose knob 34 in the other direction decreases the dosage, the processor can determine whether the dosage is being increased or decreased. By summing the number of pairs of signals that are detected by the sensor (adding increasing dosages and subtracting decreasing dosages), the processor can calculate the final dosage that has been dialed by the user.

The dosage that is set by rotation of the dose knob 32 is displayed on display 14 in the following manner. Prior to injecting a dosage of medication, the eject button 40 is depressed so that the dose knob 34 is released in preparation for the injection. When eject button 40 is depressed it activates a start button 140 on PC board assembly 22. Eject button 40 serves as a normally open switch. When eject button 40 is depressed to release the dose knob 34, the eject button 40 closes the switch (which remains closed the entire time the dose knob 34 is extended), sending an interrupt signal to a processor so that it enters a mode in which the dosage is displayed on display 14. After the dose knob 34 has been completely depressed, eject button 40 is released under the action of the eject button spring 28 and in turn opens the switch. The action of opening the switch indicates to the processor that the user has fully depressed the dose knob 34. The clutch spring 32 takes approximately 5 seconds to complete delivering the medication. The display will continue to show the dosage for a predetermined period of time after the delivery of the medication.

A memory button 95 is provided on the PC board 22 and available to the user through window 18 so that the user can review information concerning a predetermined number, e.g., five, of previous injections. Memory button 95 is a normally open switch. When the user depresses memory button 95 to close the switch, the processor causes the display 14 to enter a memory review mode, which displays the size of the previous dose and an indication of when the last dose was taken. Each time the memory button 95 is depressed the display provides the dose size and elapsed time for a previous injection. That is, if memory button is depressed four times in succession, the display will show the size of and elapsed time since the fourth previous injection. While the display may be relatively limited in the number of prior injections it can display, a data port accessible through upper body 16 can be used to download information concerning a much greater number of injections.

The memory button 95 can also be used to prevent a priming dose from being recorded. If memory button 95 is depressed while dose knob 34 is being depressed, the dose delivered will not be recorded because the processor assumes it is a priming dose. However, if the dose delivered while the memory button 95 is depressed is greater than or equal to a prescribed number of units, e.g., 4, the dose will be recorded.

What is claimed is:

1. A medication delivery pen, comprising:
   a housing having opposing proximal and distal ends;
   an actuator disposed in the proximal end of the housing for setting and administering a dosage of medication;
   a medication-containing cartridge assembly having a cartridge with a pierceably sealed distal end, an open proximal end removably attachable to the distal end of the housing, and a piston in sliding, fluid tight engagement within said cartridge;
   a drive mechanism coupled between the actuator and the cartridge to exert an axial force on the piston to inject the set dosage of medication, wherein the actuator triggers the drive mechanism to administer the injection of medication held in the cartridge;
   a processor coupled to the actuator to determine a value equal to the dosage set by the actuator; and
   means for disabling the processor when the cartridge is removed or not properly inserted in the housing,
   wherein the drive mechanism includes: a pair of half nuts in rotational engagement with the actuator; a non-rotatable lead screw having a proximal end, a distal end for exerting the axial force on the piston to inject the set dosage of medication, and a set of threads extending between the proximal and distal ends, said half nuts being radially openable and closable to selectively engage with the threads of the lead screw for axially advancing along the lead screw upon rotation of the actuator.

2. The medication delivery pen of claim 1 further comprising a first spring located in the housing and biasing the lead screw in the distal direction so that the lead screw remains in contact with the piston of the cartridge when the cartridge assembly is attached to the housing.

3. The medication delivery pen of claim 1 wherein the actuator includes a rotatable knob and a plunger in rotational engagement with the rotatable knob, said plunger having a plurality of axial splines on its distal end that define slots therebetween, said housing having at least one radially extending boss that aligns with the slots in select rotational states of the plunger to allow axial motion of the plunger and misaligns with the slots in other rotational states of the plunger to prevent axial motion of the plunger, said select rotational states of the plunger corresponding to an integer number of dosage units.

4. The medication delivery pen of claim 1 further comprising a sensor arrangement coupled to the processor for detecting rotation of the actuator.

5. The medication delivery pen of claim 4 wherein the actuator includes a rotatable knob and a plunger in rotational engagement with the rotatable knob, said plunger having an axially intermediate portion over which a plurality of radially extending splines circumferentially surrounding the plunger and wherein the sensor arrangement measures a number of rotations traveled by the plunger by detecting the number of radially extending splines that traverse a given location and generating a signal corresponding thereto, said processor receiving the signal and determining a dosage that corresponds to the number of rotations traveled by the plunger.

6. The medication delivery pen of claim 1 wherein the actuator includes a rotatable knob and a plunger, said drive mechanism including a clutch for rotationally engaging the rotatable knob with the plunger unless a torque greater than a prescribed value is applied to the rotatable knob.

7. The medication delivery pen of claim 1 further comprising means for biasing the lead screw in the distal direction so that the lead screw remains in contact with the piston of the cartridge when the cartridge assembly is attached to the housing.

8. The medication delivery pen of claim 1 further comprising means for disabling the processor when the cartridge is removed or not properly inserted in the housing.

9. The medication delivery pen of claim 1 further comprising means for preventing delivery of non-integer dosage units of medication.

10. The medication delivery pen of claim 9 wherein said delivery prevention means includes a portion of the housing that prevents axial motion of the actuator when the actuator is in select rotational states.

11. The medication delivery pen of claim 1 further comprising means for detecting rotation of the actuator and determining a dosage of medication corresponding thereto.

12. The medication delivery pen of claim 1 further comprising a display disposed on the housing for displaying at least the dosage value determined by the processor.

13. The medication delivery pen of claim 1 further comprising a memory device coupled to the processor to store at least the dosage value determined by the processor.

14. A medication delivery pen, comprising:
a housing having opposing proximal and distal ends;
an actuator disposed in the proximal end of the housing for setting and administering a dosage of medication;
a medication-containing cartridge assembly having a cartridge with a pierceably sealed distal end, an open proximal end removably attachable to the distal end of the housing, and a piston in sliding fluid tight engagement within said cartridge;
a drive mechanism coupled between the actuator and the cartridge to exert an axial force on the piston to inject the set dosage of medication, wherein the actuator triggers the drive mechanism to administer the injection of medication held in the cartridge;
a processor coupled to the actuator to determine a value equal to the dosage set by the actuator, wherein the drive mechanism includes: a pair of half nuts in rotational engagement with the actuator; a non-rotatable lead screw having a proximal end, a distal end for exerting the axial force on the piston to inject the set dosage of medication, and a set of threads extending between the proximal and distal ends, said half nuts being radially openable and closable to selectively engage with the threads of the lead screw for axially advancing along the lead screw upon rotation of the actuator; and
a release nut engaging with the lead screw at a location distally of the half nuts, said release nut being located at a first axial position when the cartridge is attached to the housing, and a second axial position when the cartridge is removed from the housing, said release nut activating the processor so that the processor is in an operational state when the release nut is in the first axial position and is in a disabled state when the release nut is in the second axial position.

15. The medication delivery pen of claim 14 wherein said release nut includes at least one tab that engages with the housing and the lead screw to prevent rotation of the lead screw.

16. The medication delivery pen of claim 14 wherein each of the half nuts have a radially extending boss engaging with an axial slot located on the distal end of the actuator, said radially extending bosses contacting an inner bearing surface of the housing when the release nut is in the second axial position to prevent further axial travel of the half nuts and so that the half nuts radially open to release the lead screw.

17. A medication delivery pen, comprising:
a housing having opposing proximal and distal ends;
an actuator disposed in the proximal end of the housing for setting and administering a dosage of medication;
a medication-containing cartridge assembly having a cartridge with a pierceably sealed distal end, an open proximal end removably attachable to the distal end of the housing, and a piston in sliding, fluid tight engagement within said cartridge;
a drive mechanism coupled between the actuator and the cartridge to exert an axial force on the piston to inject the set dosage of medication, wherein the actuator triggers the drive mechanism to administer the injection of medication held in the cartridge;
a processor coupled to the actuator to determine a value equal to the dosage set by the actuator, wherein the drive mechanism includes: a pair of half nuts in rotational engagement with the actuator; a non-rotatable lead screw having a proximal end, a distal end for exerting the axial force on the piston to inject the set dosage of medication, and a set of threads extending between the proximal and distal ends, said half nuts being radially openable and closable to selectively engage with the threads of the lead screw for axially advancing along the lead screw upon rotation of the actuator; a release nut engaging with the lead screw at a location distally of the half nuts and
at least one dial stop element coupling the distal ends of the half nuts to the release nut so that the axial travel of the half nuts is limited to a minimum value, thereby limiting the injectable dosage of medication to a minimum value.

18. The medication delivery pen of claim 17 wherein said at least one dial stop element further limits the axial travel of the half nuts to a maximum value, thereby limiting the injectable dosage of medication to a maximum value.

19. A medication delivery pen, comprising:
a housing having opposing proximal and distal ends;
an actuator disposed in the proximal end of the housing for setting and administering a dosage of medication;
a medication-containing cartridge assembly having a cartridge with a pierceably sealed distal end, an open proximal end removably attachable to the distal end of the housing, and a piston in sliding, fluid tight engagement within said cartridge;
a drive mechanism coupled between the actuator and the cartridge to exert an axial force on the piston to inject the set dosage of medication, wherein the actuator triggers the drive mechanism to administer the injection of medication held in the cartridge;
a processor coupled to the actuator to determine a value equal to the dosage set by the actuator, wherein the drive mechanism includes: a pair of half nuts in rotational engagement with the actuator; a non-rotatable lead screw having a proximal end, a distal end for exerting the axial force on the piston to inject the set dosage of medication, and a set of threads extending between the proximal and distal ends, said half nuts being radially openable and closable to selectively engage with the threads of the lead screw for axially advancing along the lead screw upon rotation of the actuator; and a radially biased eject button for locking the actuator into a depressed state after medication is injected, wherein said radially biased eject button has an inner cylindrical surface in which at least a portion of the actuator is situated, said actuator portion having a generally cylindrical shape with its distal end having a first diameter and its proximal end having a second diameter that is less than the first diameter such that the eject button is radially movable when its inner surface contacts the proximal end of the actuator portion, said actuator portion being in an extended state to trigger the drive mechanism to inject the medication and in said depressed state after the medication is injected, said distal end of the actuator portion being located in the eject button when the eject button is in its extended state so that the actuator portion cannot undergo a substantial degree of radial travel, and said proximal end of the actuator portion being located in the eject button when the eject button is in its depressed state, whereby in its depressed state the actuator portion is axially locked in position by a radial force arising from a radial displacement of the radially biased eject button.

20. A medication delivery pen, comprising:

a housing having opposing proximal and distal ends;

an actuator disposed in the proximal end of the housing for setting and administering a dosage of medication;

a medication-containing cartridge assembly having a cartridge with a pierceably sealed distal end, an open proximal end removably attachable to the distal end of the housing, and a piston in sliding, fluid tight engagement within said cartridge;

a drive mechanism coupled between the actuator and the cartridge to exert an axial force on the piston to inject the set dosage of medication, wherein the actuator triggers the drive mechanism to administer the injection of medication held in the cartridge;

a processor coupled to the actuator to determine a value equal to the dosage set by the actuator, wherein the drive mechanism includes: a pair of half nuts in rotational engagement with the actuator; a non-rotatable lead screw having a proximal end, a distal end for exerting the axial force on the piston to inject the set dosage of medication, and a set of threads extending between the proximal and distal ends, said half nuts being radially openable and closable to selectively engage with the threads of the lead screw for axially advancing along the lead screw upon rotation of the actuator; and a sensor arrangement coupled to the processor for detecting rotation of the actuator, said sensor arrangement including at least one piezoelectric film that undergoes deformation and generates an electric signal in response thereto when the actuator is rotated.

21. A medication delivery pen, comprising:

a housing having opposing proximal and distal ends;

an actuator disposed in the proximal end of the housing for setting and administering a dosage of medication;

a medication-containing cartridge assembly having a cartridge with a pierceably sealed distal end, an open proximal end removably attachable to the distal end of the housing, and a piston in sliding, fluid tight engagement within said cartridge;

a drive mechanism coupled between the actuator and the cartridge to exert an axial force on the piston to inject the set dosage of medication, wherein the actuator triggers the drive mechanism to administer the injection of medication held in the cartridge;

a processor coupled to the actuator to determine a value equal to the dosage set by the actuator, wherein the drive mechanism includes: a pair of half nuts in rotational engagement with the actuator; a non-rotatable lead screw having a proximal end, a distal end for exerting the axial force on the piston to inject the set dosage of medication, and a set of threads extending between the proximal and distal ends, said half nuts being radially openable and closable to selectively engage with the threads of the lead screw for axially advancing along the lead screw upon rotation of the actuator; and a sensor arrangement coupled to the processor for detecting rotation of the actuator, said sensor arrangement further includes a flexible planar material having a first and second opposing surfaces, a pawl extending from said first surface, and first and second piezoelectric films disposed adjacent to said second surface of the flexible planar material such that when one of the radially extending splines traverses said given location engages said pawl, said pawl deforms the flexible planar material, which in turn deforms the first and second piezoelectric films.

22. The medication delivery pen of claim 21 wherein said first and second piezoelectric films are situated with respect to said pawl such that upon deformation of the flexible planar material by the engagement between said pawl and one of the radially extending splines said first and second piezoelectric films undergo deformation with opposite curvatures.

23. A medication delivery pen, comprising:

a housing having opposing proximal and distal ends;

an actuator disposed in the proximal end of the housing for setting and administering a dosage of medication;

a medication-containing cartridge assembly having a cartridge with a pierceably sealed distal end, an open proximal end removably attachable to the distal end of the housing, and a piston in sliding, fluid tight engagement within said cartridge;

a drive mechanism coupled between the actuator and the cartridge to exert an axial force on the piston to inject the set dosage of medication, wherein the actuator triggers the drive mechanism to administer the injection of medication held in the cartridge;

a processor coupled to the actuator to determine a value equal to the dosage set by the actuator; and a sensor arrangement coupled to the processor for detecting rotation of the actuator, said sensor arrangement including at least one piezoelectric film that undergoes deformation and generates an electric signal in response thereto when the actuator is rotated.

* * * * *